United States Patent
Redha et al.

(10) Patent No.: US 10,856,874 B2
(45) Date of Patent: Dec. 8, 2020

(54) DEVICE FOR CONNECTING HOLLOW ORGANS, ESPECIALLY BLOOD VESSELS, BY SURGERY

(71) Applicant: King Faisal Specialist Hospital & Research Centre, Riyadh (SA)

(72) Inventors: Falah Redha, Bern (CH); Essam Al Shail, Riyadh (SA)

(73) Assignee: King Faisal Specialist Hospital and Research Center, Riyadh (SA)

( * ) Notice: Subject to any disclaimer, the term of this patent is extended or adjusted under 35 U.S.C. 154(b) by 297 days.

(21) Appl. No.: 15/901,626

(22) Filed: Feb. 21, 2018

(65) Prior Publication Data

US 2018/0185027 A1    Jul. 5, 2018

Related U.S. Application Data

(62) Division of application No. 13/972,452, filed on Aug. 21, 2013.

(51) Int. Cl.
*A61B 17/11*   (2006.01)
*A61B 17/00*   (2006.01)

(52) U.S. Cl.
CPC ..... *A61B 17/11* (2013.01); *A61B 2017/00535* (2013.01); *A61B 2017/1107* (2013.01); *A61B 2017/1121* (2013.01); *A61B 2017/1132* (2013.01)

(58) Field of Classification Search
CPC ............ A61B 17/11; A61B 2017/1107; A61B 2017/1121; A61B 2017/1132; A61B 2017/1135; A61B 2017/1139

USPC ......................................... 606/149, 151, 153
See application file for complete search history.

(56) References Cited

U.S. PATENT DOCUMENTS

| | | | |
|---|---|---|---|
| 1,151,300 A | 8/1915 | Soresi |
| 2,453,056 A | 11/1948 | Zack |
| 2,779,996 A | 2/1957 | Tanis |
| 2,940,451 A | 6/1960 | Vogelfanger |
| 2,940,452 A | 6/1960 | Smialowski |
| 3,040,748 A | 6/1962 | Klein |
| 3,048,177 A | 8/1962 | Takaro |
| 3,180,337 A | 4/1965 | Smialowski |
| 3,221,746 A | 12/1965 | Noble |
| 3,254,650 A | 6/1966 | Collito |
| 3,254,651 A | 6/1966 | Collito |
| 3,774,615 A | 11/1973 | Sprincl |

(Continued)

FOREIGN PATENT DOCUMENTS

GB    1413191    11/1975

OTHER PUBLICATIONS

Office Action for U.S. Appl. No. 13/972,452, dated May 16, 2019.
(Continued)

*Primary Examiner* — Diane D Yabut
*Assistant Examiner* — Majid Jamialahmadi
(74) *Attorney, Agent, or Firm* — Pearl Cohen Zedek Latzer Baratz LLP

(57) ABSTRACT

A sleeve for enforcing the end of a hollow organ so that it can be connected with a further end of a hollow organ, the sleeve comprising a cylindrical shape and being configured to be pushed over the end of the hollow organ and for turning-over the end of the hollow organ projecting from the sleeve around an end of the sleeve, wherein the sleeve has an adjustable diameter.

10 Claims, 6 Drawing Sheets

(56) References Cited

U.S. PATENT DOCUMENTS

| | | | |
|---|---|---|---|
| 4,016,883 | A | 4/1977 | Wright, Jr. |
| 4,055,186 | A | 10/1977 | Leveen |
| 4,165,747 | A | 8/1979 | Bermant |
| 4,366,819 | A | 1/1983 | Kaster |
| 4,474,181 | A | 10/1984 | Schenck |
| 4,624,255 | A | 11/1986 | Schenck |
| 7,955,342 | B2 | 6/2011 | Alshail |
| 2002/0173802 | A1 | 11/2002 | Schulze |
| 2004/0199189 | A1 | 10/2004 | Bolduc |
| 2005/0143758 | A1 | 6/2005 | Abbott |
| 2006/0004391 | A1 | 1/2006 | Haverich et al. |
| 2007/0073317 | A1 | 3/2007 | Tanaka |
| 2008/0009936 | A1 | 1/2008 | Kim et al. |
| 2009/0131957 | A1* | 5/2009 | Redha .................. A61B 17/11 606/153 |
| 2009/0259306 | A1 | 10/2009 | Rowe |
| 2010/0174300 | A1 | 7/2010 | Blondeel |
| 2010/0324653 | A1 | 12/2010 | Rubenstein |
| 2012/0277774 | A1 | 11/2012 | Guo |
| 2013/0012969 | A1 | 1/2013 | Shin |
| 2014/0052160 | A1 | 2/2014 | Singh et al. |

OTHER PUBLICATIONS

Office Action for U.S. Appl. No. 13/972,452, dated Apr. 4, 2018.
Final Office Action for U.S. Appl. No. 13/972,452, dated Aug. 30, 2019.

\* cited by examiner

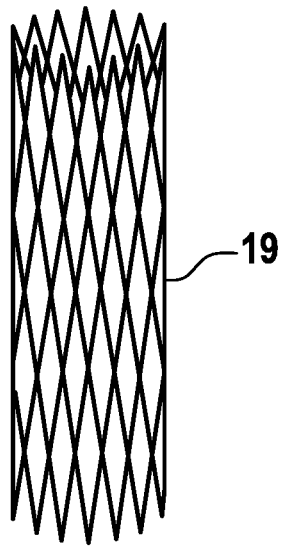
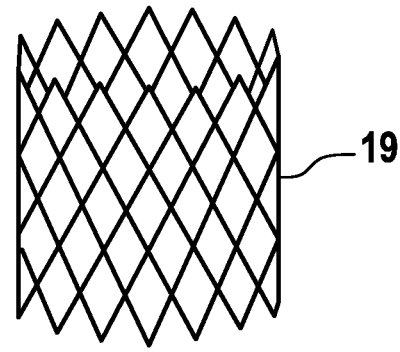
Fig. 1a Fig. 1b
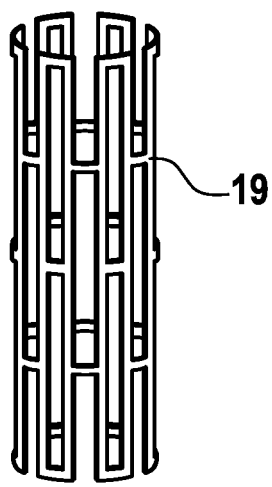
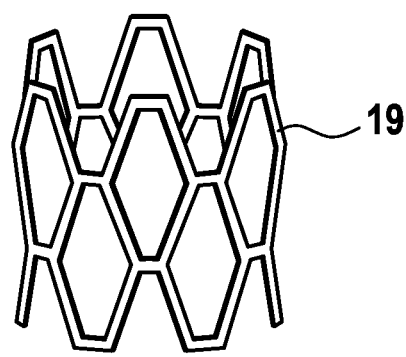
Fig. 2a Fig. 2b

DEVICE FOR CONNECTING HOLLOW ORGANS, ESPECIALLY BLOOD VESSELS, BY SURGERY

CROSS REFERENCE TO RELATED APPLICATIONS

This application is a divisional of U.S. patent application Ser. No. 13/972,452, filed on Aug. 21, 2013, which is incorporated herein by reference in its entirety.

FIELD OF THE INVENTION

The invention relates to a device for the anastomosis of hollow organs.

BACKGROUND OF THE INVENTION

One important task in surgery is end-to-end anastomosis. In the text which follows, this should be understood to mean in particular the surgical connection of blood vessels. However, the techniques described below can in principle also be used for the anastomosis of any hollow organ ends.

In end-to-end anastomosis, stitching is the most frequently used connection technique. However, instead of stitching, which takes a lot of time, the connection can also be achieved in a fraction of the time by using fittings and sleeves. For this purpose, a sleeve which is preferably biodegradable is pushed over each of the two vessel ends. The inner diameter of said sleeve must correspond approximately to the outer diameter of the vessels. The sleeve is in each case pushed over the vessel until the end of the vessel protrudes slightly out of the sleeve. The end of the vessel then has to be turned over around the end of the sleeve so that the sleeve is secured and the inner side of the vessel, the tunica intima, is facing outwards. The two sleeves are then pushed into a third fitting and are fixed in the latter in such a way that the inner sides of the two vessels make contact with one another around the entire circumference. This is necessary in order for the two vessel ends to be able to grow together.

During this procedure, the work of the surgeon can be facilitated by various auxiliary means, for example by using devices which hold and clamp the ends of the blood vessels, which hold fittings and help to align these with one another in the axial direction, which make it easier to push the fittings together, or by using a device which assists and facilitates the process of turning the ends of the blood vessels over around the ends of the fittings.

Many auxiliary means for the anastomosis of vessels have already been known for decades. U.S. Pat. Nos. 4,474,181 and 4,624,255 disclose a device which consists essentially of a ring having a diameter larger than the outer diameter of the blood vessel. The vessel ends to be connected are firstly stitched together at least at three points. The ring is then pushed over the stitching area. Using the threads of the stitches, the vessel is widened to the diameter of the ring and is fixed to the ring in this position. As a result, the inner sides of the two vessels are brought into contact with one another. U.S. Pat. Nos. 4,016,883 and 4,165,747 contain examples of clamps, especially for blood vessels having a small diameter. U.S. Pat. No. 4,165,747 moreover proposes clamps which are arranged in a displaceable manner on a common rail. In this way, the blood vessels can be simultaneously clamped and can be fixed in position relative to one another; this makes it easier to stitch them together.

Further devices which ensure the mutual axial alignment of the vessel ends and fittings are described in U.S. Pat. Nos. 1,151,300, 2,940,451 and 3,048,177. In all cases, at least one vessel end must be turned over around a sleeve prior to the connection operation so that the inner sides of the two vessels make contact with one another after being joined.

Unlike the abovementioned patent specifications, U.S. Pat. No. 2,453,056 describes how the turning-over of the vessel ends is achieved, namely by using tweezers. It is known that it is very difficult to turn vessels over using a number of pairs of tweezers, and this process sometimes requires more than one person. Even if the surgeon is assisted by a mechanical device which is able to hold and guide a number of pairs of tweezers or grippers in a suitable manner, there is still the risk that the vessel ends will be damaged during the manipulations.

U.S. Pat. No. 2,453,056 demonstrates that the use of sleeves or fittings as auxiliary means for anastomosis has already been known for a very long time. U.S. Pat. Nos. 3,221,746, 3,254,650, 3,254,651, 3,774,615, 4,366,819 or U.S. Patent Appl. Publ. No. 2004/0199189 A1 also propose the use of fittings. However, a difficulty using sleeves and fittings is that basically for each hollow organ a specific sleeve and fitting has to be provided with diameters corresponding to the hollow organ it is used with.

Various auxiliary means have also been developed for turning the vessel ends over around the end of a sleeve. GB 1413191 proposes a number of spikes which are formed on the outside of the sleeve and can be moved in the axial direction. They have barbs pointing outwards and protrude slightly beyond the end of the sleeve. The edge of the vessel, which has previously been pushed through the sleeve, is pulled and respectively pushed onto the barbs by means of tweezers. The spikes are then retracted. The vessel end is thus pulled over the end of the sleeve.

U.S. Pat. No. 2,940,452 proposes the use of an elastomer membrane. The latter is pulled taut over the end of a tube. A cylindrical piston with a conical end is then pushed forward through the interior of the tube until the membrane has a conical bulge. In this position, the piston with the membrane pulled taut over it is pushed into the end of the blood vessel protruding beyond a sleeve and then is pressed against the sleeve. The outer tube is then pushed in the direction of the vessel. In the process, the membrane is placed around the end of the sleeve, and with it the protruding part of the blood vessel.

U.S. Pat. No. 3,180,337 describes a similar device, but without the membrane. A cylindrical piston with a conical end is again used. The cylindrical part of the piston is surrounded by an axially displaceable tubular part made of elastic material. Firstly, the conical end of the piston is pushed into the end of the blood vessel protruding beyond a sleeve and then is pressed against the sleeve. The aforementioned tubular piece is then pushed over the piston in the direction of the blood vessel. The tubular piece firstly upsets the protruding end of the blood vessel, then widens together with the end of the blood vessel, and finally both are turned over around the end of the sleeve.

U.S. Pat. No. 2,779,996 describes an elastic ring as an auxiliary means, which is pushed into the interior of the protruding part of the vessel end. After being inserted, the ring—and thus also the protruding part of the vessel—is widened by means of compressed air, and in this way the protruding part of the vessel end is turned over around the sleeve.

The device according to U.S. Pat. No. 3,040,748 is similar to the auxiliary devices in U.S. Pat. Nos. 2,940,452 and 3,180,337. It uses a cylindrical piston with a conical end in a known manner. A thin tubular piece made of an elastic material is pulled on behind the conical head. The rear end of this tube has a bead. It is held by a further tube which can be displaced in the axial direction, and is already widened. In a known manner, the piston with the conical end is pushed into the protruding part of the blood vessel and then pressed against the sleeve. This operation is assisted by a fluid which is pumped through the tip of the conical piston head into the clamped vessel. The fluid flows between the vessel and the piston and also through the tubular piece made of elastic material, and thus makes it easier to push the vessel end onto the tubular piece. Once it has been pushed on, the flow of fluid is stopped. The outer, displaceable tube is then pushed in the direction of the sleeve. It takes with it the elastic tubular piece—and thus the vessel end pushed over the latter—and turns both of these over around the sleeve.

U.S. Pat. No. 4,055,186 describes a press-fastening system for joining two parts of an intestine. Attached to both parts of the press fastener is a concentric ring which is mounted in a flexible manner in the axial direction. The rings have an outer diameter which is somewhat smaller than the inner diameter of the intestine parts to be connected. The press-fastener parts with the rings are pushed into the ends of the intestine parts and then the latter are turned over inwards around the rings. There is no description as to how this is to be achieved. The press-fastener parts are then joined and latched together. Thanks to the flexible rings, the two intestine parts are pressed against one another with a defined force.

U.S. Pat. No. 7,955,342 describes a device for connecting hollow organs comprising various elements that are held by holding devices. Said holding devices can be laterally displaced on a slide rail, rotated or detached and put on, and their position can be secured, if required. The traverse is used as a stop for the axial alignment of the holding devices. The holding devices carry clamping devices for retaining and, if required, clamping off the hollow organ ends. The holding devices carry fittings. The two hollow organ ends to be connected are pushed through the fittings to such an extent as to project over the fitting ends by a defined extend. The ends of the hollow organs are then turned up by the ends of the fitting using two turn-up devices. The holding device in the center holds an additional fitting into which the two fittings are inserted with the turned-up hollow organ ends and are secured.

U.S. Patent Appl. Publ. No. 2010/0174300 A discloses a method for performing end-to-end vessel anastomosis including providing a vessel support including a vessel receiving portion and a handle portion extending therefrom. The vessel receiving portion is an annulus. The vessel receiving portion is positioned around the end of a first vessel and the end of the first vessel is everted about the outer diameter of the vessel receiving portion such that the inner surface of the vessel is directed outwardly. The end of the second vessel is positioned over the everted end of the first vessel such that the inner surface of the second vessel is disposed against the inner surface of the first vessel. The ends of the vessel are secured either with a suture or a surgical adhesive. The handle portion of the vessel support may be removed.

U.S. Patent Appl. Publ. No. 2005/0143758 discloses anastomosis devices for fixing a first conduit to a second conduit in an anastomosis, where the conduits are joined by interfacing their inner walls together. The conduit which is loaded on the anastomosis device may be mounted in such a way that the internal wall of the conduit does not make contact with the anastomosis device.

U.S. Patent Appl. Publ. No. 2013/0012969 discloses a stent for connecting adjacent tissues of the organs of a patient. The stent includes a hollow cylindrical body which is formed by weaving a superelastic shape-memory alloy wire in an overlapping manner such that rhombic openings are formed, and wing parts which are provided by expanding respective opposite ends of the hollow cylindrical body outwards and turning the opposite ends inside out on bent portions. The wing parts face each other so that the wing parts are tensed in a longitudinal direction of the cylindrical body. Thereby, the wing parts can elastically move inwards or outwards with respect to the longitudinal direction to automatically adjust a distance between the wing parts in response to the distance between the adjacent tissues of the organs or thicknesses of walls of the organs, so that the wing parts are put into close contact with the adjacent tissues.

All the aforementioned devices for the anastomosis of blood vessels have certain drawbacks with regard to handling or their function. The object of the invention is therefore to find improved devices for anastomosis without the drawbacks of the prior art.

SUMMARY OF THE INVENTION

According to the invention, this object is achieved by a sleeve, a fitting, a turning-over device for turning-over the end of a hollow organ around the end of a sleeve and a method, all as claimed.

Further advantageous embodiments are described in the dependent claims.

The sleeve according to the invention is a sleeve for enforcing the end of a hollow organ so that it can be connected with a further end of a hollow organ. It comprises a cylindrical shape. The sleeve is configured to be pushed over the end of the hollow organ and for turning-over the end of the hollow organ projecting from the sleeve around an end of the sleeve. The sleeve according to the invention has an adjustable diameter.

The sleeve according to the invention having an end of a hollow organ folded back over its end stabilizes and re-enforces the end of the hollow organ so that it can be brought in contact with another end of a hollow organ which has been prepared in the same way and can be fixed in a contact relation with the other hollow organ end by a fitting provided around or grasping the sleeves with the two hollow organ ends secured to them.

Due to its adjustable diameter the sleeve may be adjusted to different outer diameters of hollow organs. Hence the sleeve is suitable for a use with multiple hollow organs having different diameters.

According to one embodiment, the sleeve is formed by an expandable material mesh that is configured so that its diameter can be adjusted by applying a pressure, particularly a radial pressure. The mesh can be a self-expandable material mesh that is formed by weaving filaments or by punching or etching a material layer to form multiple filaments that are connected with each other at nodes. According to a further embodiment, the sleeve is composed of fine metallic or non-metallic filaments. According to another embodiment the filaments have the shape of elongate members or wires, and the filaments may be fixedly secured to one another where the filaments intersect with one another. The filaments may be fixed to one another by welding. The filaments may have a cylindrical, triangular, square, rectangular or hexagonal etc. cross-section. According to still another embodiment of the present invention the filaments may be thin bars which can have a square, or rectangular cross-section. Preferably, the filaments are fixedly secured to one another where the bars intersect with one another. The sleeve may have a rhomb-shaped or rectangle-shaped pattern of filaments in the unstressed state or under pressure.

According to yet a further embodiment, the sleeve is configured so that it reduces its diameter or collapses by applying a radial pressure, and returns to its original diameter when the pressure is released or returns to a reduced diameter if a reduced pressure is exerted. Hence, the sleeve can be adjusted to hollow organs with different diameters. The adjustability of its diameter facilitates the positioning of the sleeve on the hollow organ, since it may be pushed on the hollow organ with a larger diameter, while the diameter of the sleeve can be adjusted to the outer diameter of the hollow organ by applying a corresponding radial pressure, once the sleeve is correctly positioned. When the end of the hollow organ is folded back on the sleeve it is kept at its reduced diameter by the back-folded hollow organ end.

According to another embodiment the sleeve comprises a region having a reduced diameter and at least one other region which comprises a larger diameter. The shape of the sleeve may be preformed in this manner and conserves this geometry without any pressure being applied. The geometry facilitates the pushing and positioning of the sleeve on the end of the hollow organ.

According to a further embodiment the sleeve has a constant diameter over its length without any pressure being applied and a region having a reduced diameter when a radial pressure is exerted on the sleeve in that respective region, wherein at least one other region of the sleeve comprises a larger diameter when no pressure or a lower radial pressure is exerted on the sleeve.

According to a further embodiment the region having a reduced diameter includes one end of the sleeve where a hollow organ end is folded back on the sleeve, wherein the pressure is exerted on the region of the sleeve by the folded back hollow organ end.

According to yet another embodiment the edge of the mesh can be configured so that the end of the hollow organ easily turns over the sleeve and remains there in a fixed position. In particular, the edge of the mesh at the end of the sleeve is sharp. The edge may also be continuous. Furthermore, a section of the sleeve at at least one end of the sleeve may have a frustoconical shape, i.e. may have an increasing diameter over a region at its end in order to support the folding back of the end of the hollow organ projecting from the sleeve.

According to another embodiment one or both ends of the sleeve are provided with spikes radially extending from the sleeve, wherein the spikes are configured to fix the turned-over hollow organ end additionally on the sleeve.

According to yet another embodiment the spikes extend from the sleeve at an angle between 5 degrees and 175 degrees with regard to the longitudinal axis of the sleeve. In particular, the spikes may extend with an angle from the group including 5, 10, 20, 30, 40, 50, 60, 70, 80, 90, 100, 110, 120, 130, 140, 150, 160, 170, and 175 degrees or an angle in one of the ranges defined between the angles of the above group.

According to a further embodiment the spikes are formed by filaments of a material mesh forming the sleeve and extend from a region at the end of the sleeve.

According to a still another embodiment the spikes formed by filaments of the material mesh are configured to vary their angle of extension from the sleeve in dependence of the diameter of the sleeve. In particular, the filaments may be configured so that the angle of extension of the spikes is at a minimum with regard to the longitudinal axis of the sleeve when the sleeve has its maximum diameter, for example, when no pressure is applied and the angle of extension of the spikes is at a maximum with regard to the longitudinal axis of the sleeve, when the sleeve has a larger diameter, for example, when a pressure is applied that fits the diameter of the sleeve to the outer diameter of the hollow organ. The minimum angle of extension of the spikes may by in a range between −10 and 10 degrees, in particular the angle can be zero degrees with regard to the longitudinal axis of the sleeve, or some other suitable angle, and the maximum angle of extension of the spikes may by any angle of the group indicated above.

According to a further embodiment, the inner side of the sleeve for accommodating the end of the hollow organ has a surface structure which increases the static friction when the hollow organ is pressed against the inner side of the sleeve but which at the same time does not substantially hinder the insertion of the hollow organ into a fitting. This surface structure may be achieved with spikes that can be similar to the spikes described above, wherein the spikes are oriented in a direction that permits to push the sleeve on the hollow organ but hinders a movement in the opposite direction. The spikes on the inner surface of the sleeve can be formed by some filaments of the mesh. The angles indicated above with regard to the spikes that extend radially outward from the sleeve are also applicable for the inner spikes. According to another embodiment the sleeve can also comprise a roughened inner surface.

According to yet another embodiment, the sleeve for accommodating the hollow organ end has at least one groove or bead running around the entire outer circumference or inner circumference. In the case of a sleeve that is formed by a material mesh, the groove or bead can be formed in the mesh. The groove or bead facilitates the holding of the sleeve in a fitting that accommodates for example two sleeves with hollow organ ends in a position in which the inner sides of the hollow organ ends are in contact with each other.

According to yet another embodiment the sleeve is formed of a stainless metal, steel, alloy, a biodegradable material, in particular, a biodegradable plastic, or a biocompatible material such as biocompatible plastic, a memory shape alloy metal or a material comprising several of these properties or any other suitable material.

The invention also includes a fitting for receiving and fixing at least one sleeve according to one of the embodiments described above that is configured to receive and hold two sleeves with turned-over hollow organ ends so that the inner sides of the hollow organ ends make contact with one another. The fitting supports the adhesion of the hollow organ ends. By means of the fitting, a re-connected and re-established hollow organ may be achieved. The fitting has a generally cylindrical shape.

According to an embodiment the fitting for accommodating the two sleeves is completely or partially slit in the longitudinal direction. This allows or facilitates the insertion of the two sleeves with the turned over hollow organ ends.

According to yet another embodiment the fitting is a ring that is completely or partially slit in the longitudinal direction. According to a further embodiment the fitting comprises a fenestration that permits to observe the ends of the hollow organs introduced into the fitting. Alternatively, the fitting may be formed of a transparent material, i.e. transparent plastic or biocompatible or biodegradable transparent plastic that permits the observation of the hollow organ ends encompassed and covered by the fitting.

According to still another embodiment the fit of the sleeve for accommodating the hollow organ end and of the fitting for accommodating two sleeves allows a press fit, an interference fit or a push fit.

According to still another embodiment the fitting comprises a curved profile or a U-profile along its longitudinal axis which permits the fitting to encompass two sleeves with turned-over hollow organ ends preferably over their entire lengths, wherein the inner sides of the hollow organ ends make contact with one another. The fitting may have annular end walls at its ends that extend substantially perpendicular to the longitudinal axis of extension of the fitting. The end walls comprise a diameter that is smaller than the inner diameter of the fitting so that the end walls can contribute to hold a sleeve in the fitting. According to an embodiment the fitting has a length that corresponds to about the double length of a sleeve so that the fitting can accommodate two sleeves with back folded hollow organ ends.

According to an embodiment, the fitting may be formed of metal or plastic material. In particular, the fitting may be formed of a biodegradable plastic or of biocompatible plastic or may be formed of magnesium that is covered by a biodegradable plastic.

According to yet another embodiment, the fitting for accommodating the two sleeves is split in the center, wherein the two parts are connected via an axially flexible central part so that, after the latching-in of the sleeves, a defined force is exerted on the turned-over hollow organ.

According to another embodiment, the fitting for accommodating two sleeves has at least one, but preferable two beads or grooves running around the entire inner circumference into which corresponding grooves or beads of the sleeves can latch. The grooves or beads may also partially extend around the inner circumference of the fitting.

According to the invention, a turning-over device is provided for turning over the end of a hollow organ around the end of a sleeve, wherein said turning-over device comprises a front part consisting of a pin having a diameter which corresponds approximately to the inner diameter of the hollow organ and a rear part having a diameter which is larger than that of the front part, wherein the rear part comprises a fluid connection to at least one outlet of the device for a fluid that during the turning-over process is pressed out of said outlet, wherein said outlet is formed in a sidewall of said pin, wherein the fluid is pressed out of said pin at least partly under a nonzero angle in relation to the axis of extension of said pin.

It is one of the benefits of the turning-over device of the invention that it permits to turn over the end of a hollow organ, in particular, a blood vessel around the end of a sleeve in a fast and reliable manner. The turning-over device of the invention can be used for turning over the end of two related sections of hollow organs, in particular, blood vessels, in order to subsequently bring them into contact with each other to re-establish the hollow organ, in particular, blood vessel.

According to one embodiment, the pin of the device comprises an essentially rotationally symmetrical body, and the outlet is formed in a sidewall of said rotationally symmetrical body. Such a shape of the pin provides for an easy insertion of the front part of the turning-over device into the hollow organ. The tip of the pin may also be rounded. Since the outlet is formed in a sidewall of the pin, a stream of pressurized fluid may be directed on the inner wall of the end of the hollow organ in order to support the turning-over of the hollow organ end on a sleeve arranged on the hollow organ.

According to another embodiment, the outlet has the shape of a slit that extends perpendicularly to the axis of symmetry of said pin over more than half of its periphery. Preferably, the outlet extends over the entire periphery of the pin, so that an annular outlet is formed through which pressurized fluid can be output homogenously on the entire internal periphery of the end of the hollow organ in order to facilitate and effect the turning-over process. In accordance with the annular shape of the outlet, the ejected jet of fluid may have a circular shape as well. According to yet another embodiment, the annular outlet can be interrupted by solid sections or bars in the pin resulting in several slit shaped outlet sections arranged around the periphery of the pin along a circle.

According to another embodiment, the pin comprises several outlets distributed over its surface wherein at least one, several or all outlets are configured in a way so that a fluid is pressed out of the at least one outlet, the several outlets under a non-zero angle in relation to the axis of symmetry of the pin.

The outlets may be distributed equally over the pin, particularly, in a circular section of the pin, or they can be located in two or more opposite sections on the pin or also in a single section on one side of the pin or can be located in a larger number of sections on the pin. Additionally, an outlet may be provided in the tip of the pin from which the pressurized fluid is ejected essentially in the direction of the longitudinal axis of the pin. The shape of the outlets may be circular, oval or rectangular. Furthermore, outlets with different diameters may be combined on one pin. Also, the width of an outlet that has the shape of a slit may vary over the pin. For example, the width of an annular slit may be larger at two opposite sections of the pin, while it is smaller at the two opposing sections between the opposing sections with the larger slit width. Also a combination of outlets with different shapes or sizes may be provided on the pin.

According to a further embodiment, the device is configured so that the mean angle, at which the fluid exits from the at least one outlet with relation to the longitudinal axis of extension of said pin is between 10 and 90 degrees. The angle under which the pressurized fluid exits the outlet may depend on the shape and the orientation of the conduits in the pin for supplying the pressurized fluid to the at least one outlet. Specific angles under which the fluid may exit the at least one outlet include 10, 20, 30, 40, 50, 60, 70, 80 and 90 degrees or any angles or ranges between these angles. The diameter of the conduits may be constant over the length of the conduits or may vary. The device may include one or several conduits having a conical shape at least in a section of their length. The conical shape may have a pressurizing effect on the fluid.

According to yet another embodiment, the at least one outlet is positioned at a predetermined distance along the length of the pin, wherein the pin is configured to be pushed into the opening of the hollow organ so that the at least one outlet is covered by the hollow organ when the edge of the hollow organ is pushed over the pin towards the rear part of the device. The distance between the outlet in the pin and the beginning of the rear part of the device may approximately correspond to the maximum length of the hollow organ end that can be turned over and folded back on the sleeve.

According to a further embodiment, the position of the at least one outlet is provided at a pre-determined distance from the distal end of the pin which defines the distance along which the hollow organ can be clamped between the pin and the sleeve that has been pushed over the hollow organ up to about the outlet in the pin. Since the outer diameter of the pin basically corresponds to the inner diameter of the hollow organ and a sleeve has been provided on the hollow organ in a section of the pin between the tip of the pin and the at least one outlet, the hollow organ can be fixed between the pin and the sleeve, in particular, due to friction between these elements. Preferably, the pin is inserted into the hollow organ at most to a position where the outlet in the pin is not covered by the sleeve on the hollow organ so that the end of the hollow organ can be turned over and folded on the sleeve by the pressurized fluid exiting the outlet.

According to still another embodiment, the pin comprises a central conduit that essentially extends in its longitudinal direction to connect the front part of the device with its rear part wherein the central conduit branches off in at least on branch conduit that is connected with the at least one outlet.

According to another embodiment, the branch conduit branches off from the central conduit in direction of the distal end of the pin with an angle between 10 and 90 degrees in relation to the longitudinal axis of the pin. Due to the tilted arrangement of the branch conduit in the pin, the exit of pressurized fluid with a defined angle in relation to the longitudinal axis of the pin can be achieved so that the fluid directly strikes the inner wall of the hollow organ end in order to turn it over. Specific angles of the branch conduit in relation with the pin axis include 10, 20, 30, 40, 50, 60, 70, 80, 90 degrees, or any angles or ranges between these angles.

According to an embodiment the central conduit and the branch conduit comprise a straight shape. However, curved shapes for one or several conduits may also be conceived. Furthermore, in case the pin includes several outlets, separate branch conduits may be provided connecting the central conduit with the individual outlets. The device may even include several central conduits.

According to a further embodiment, the front side of the rear part of the device facing towards the opening of the hollow organ has a concave part. The concave part can be provided as a extension at the proximal end of the pin and may comprise a rotational symmetry around the longitudinal axis of the pin. The concave part facilitates the turning-over of the end of the hollow organ and may also widen the end of the hollow organ when the pin is pushed in the hollow organ.

According to another embodiment the concave part may have a U-shaped cross-section. At the side opposing the pin the concave part may extend as a wall that extends parallel to the pin, wherein an annular groove is formed between the wall and the pin. The concave part may have a semicircular cross-section. The depth of the groove may correspond to the radius of the semicircular cross-section of the concave part. However, the ratio between the depth of the groove and the radius of the semicircular cross-sectional profile of the concave part may also have a factor of 1.5, 2.0, 2.5, 3.0, 3.5, 4.0, 4.5, 5.0, a value in a range between these numbers or a larger value. The depth of the groove may be in a range between 2 and 8 mm depending on the diameter of the hollow organ or blood vessel.

According to an embodiment one or several outlets for pressurized fluid may be provided in the concave part. An outlet may be provided that comprises an annular shape that may be centralized with regard to the axis of symmetry of the pin. According to another embodiment several outlets may be arranged on a circular line around the axis of symmetry of the pin.

According to still another embodiment, the rear part of the device comprises a reservoir for the fluid, wherein said rear part has an opening through which said fluid in said reservoir can be pressurized. A means for pressuring the fluid in the reservoir can be a syringe, a catheter or a pump connected to the opening in the rear part.

According to the invention, a method of connecting two hollow organs with a sleeve and a device according to the invention as described above is provided, wherein the method comprises steps of pushing the sleeve over the end of the first hollow organ so that a pre-determined length of the hollow organ projects from the sleeve, pushing the device for turning over the end of the hollow organ around the end of the sleeve with its front part into the opening of the hollow organ until the end of the hollow organ surrounds the pin of the front part and covers the outlet; pressing a fluid through the outlet in the pin under a non-zero angle in relation to the longitudinal axis of the pin on the inner wall of the end of the hollow organ, wherein said pressurized fluid exiting from the outlet strikes the hollow organ and turns over the end of the hollow organ over the sleeve.

The method according to the invention facilitates the generally difficult task of turning over a hollow organ such as a blood vessel over a sleeve in order to connect two ends of hollow organs at their inner sides in order to re-establish the closed hollow organ.

According to another embodiment, the two ends of hollow organs provided with sleeves each having turned-over hollow organ ends are introduced into a common fitting so that the ends of the hollow organs make contact with another and the hollow organ ends are fixed in the fitting. With a fitting that is slit in the longitudinal direction, the insertion of the two sleeves can easily be provided.

When using a sleeve with an adjustable diameter such as a sleeve formed of a self-expandable mesh, the diameter of the sleeve can be exactly adjusted to the outer diameter of the hollow organ so that a stable and strong connection of the hollow organ end, which is folded over on the sleeve, can be achieved.

According to yet another embodiment, the method comprises clamping off the hollow organ behind the sleeve before the pressurized fluid exits the outlet and until the end of the hollow organ has been turned over around the end of the sleeve. Clamping off the hollow organ has the effect that pressurized fluid which enters the hollow organ through the outlet in the pin increases the pressure in the hollow organ so that the friction between the hollow organ and the sleeve is increased in order to facilitate the turning-over of the hollow organ end and to avoid a pushing-back of the hollow organ from the sleeve and the device due to the pressure of the pressurized fluid.

BRIEF DESCRIPTION OF THE DRAWINGS

Further embodiments and advantages of the invention will become apparent from the following description of preferred embodiments of the invention with reference to the drawings, wherein:

FIGS. 1a, 1b show a sleeve for enforcing the end of a hollow organ according to one embodiment of the invention;

FIG. 2a, 2b show a sleeve for enforcing the end of a hollow organ according to another embodiment of the invention;

DETAILED DESCRIPTION OF THE INVENTION

FIGS. 1a and 1b and FIGS. 2a and 2b show sleeves 19 according to a particular embodiment of the invention. The sleeves 19 comprise a cylindrical shape and are formed of a material mesh comprising a shape-memory alloy material. The sleeves 19 have an adjustable diameter. FIGS. 1a and 2a show the mesh structure of the sleeve 19 in a compressed state when a pressure, in particular a radial pressure is exerted on the sleeve 19 as, for example, by forceps and FIGS. 1b and 2b show the mesh structure of the sleeve 19 in an expanded state without any pressure or a reduces pressure exerted. The sleeves 19 can be formed of a shape-memory allow material, such as Nitinol, of stainless steel or of a biodegradable material. Releasing the pressure exerted on the sleeves 19 in FIGS. 1a and 2a, the sleeves expands to a larger diameter as is shown in FIGS. 1b and 2b. The sleeve 19 shown in FIGS. 1a and 1b is formed of fine filaments having a cylindrical cross-section, wherein the filaments are connected with each other at the crossing points by welding. The sleeve 19 comprises a rhomb shaped mesh pattern. The sleeve 19 shown in FIGS. 2a and 2b is formed of bar-shaped filaments having a flat rectangular cross-section. The sleeve 19 has a rectangular mesh pattern as is visible in FIG. 2a. The sleeve 19 may be formed by punching or etching a thin material layer of a suitable material such as stainless steel, Nitinol, gold, etc. Alternatively, the sleeve 19 may be formed by welding of filaments.

Figure 2C:
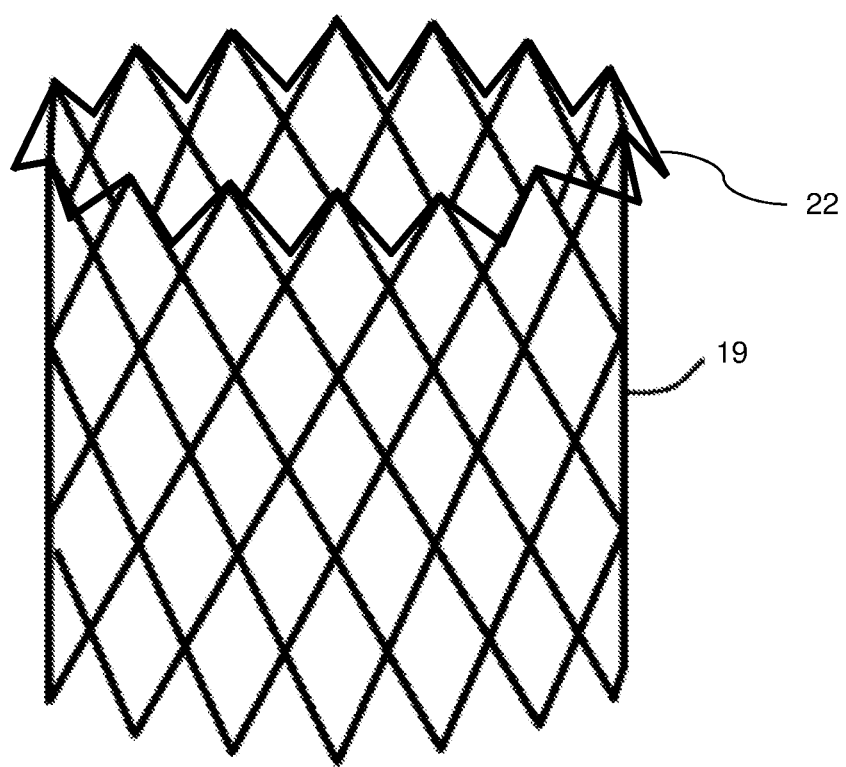
FIG. 2c shows a sleeve having spikes radially extending from the sleeve, according to one embodiment of the invention.
Figure 3A:
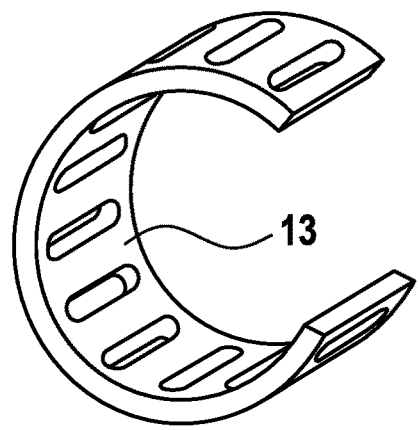
FIGS. 3a-d show a fitting according to one embodiment of the invention in (a) a first open state, (b) arranged around two hollow organ ends provided with sleeves in an open state, (c) in a closed state and (d) arranged around two hollow organ ends in a closed state.
Figure 3B:
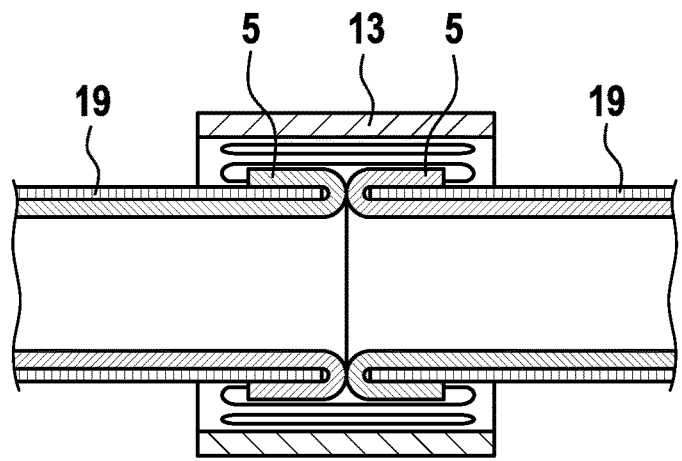
Figure 3C:
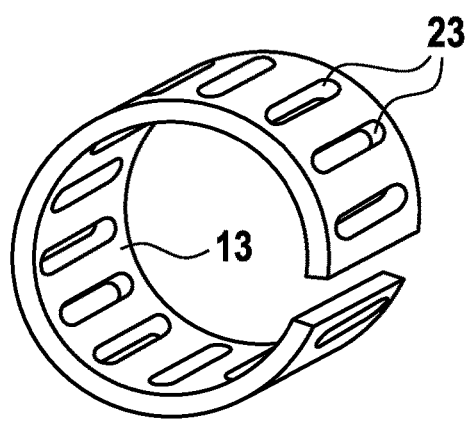
Figure 3D:
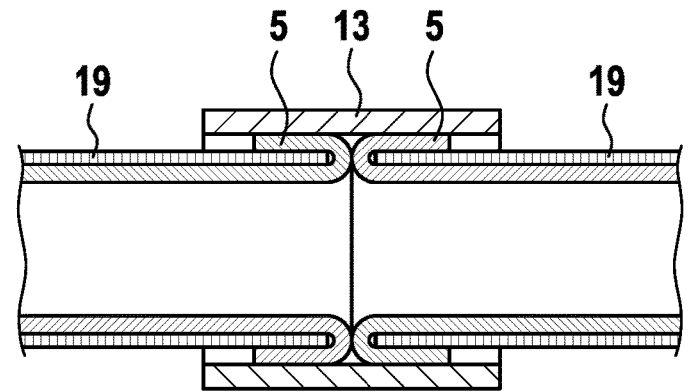

FIG. 2c shows sleeve 19 having spikes 22 radially extending from one end of sleeve 19, according to one embodiment of the invention. One or both ends of the sleeve may be provided with spikes 22 radially extending from the sleeve 19, wherein the spikes 22 are configured to fix the turned-over hollow organ 5 end additionally on the sleeve 19. The spikes 22 can extend from the sleeve 19 at an angle between 5 degrees and 175 degrees with regard to the longitudinal axis of the sleeve 19. According to a further embodiment, as shown in FIG. 2c, the spikes 22 are formed by filaments of a material mesh forming the sleeve and extend from a region at the end of the sleeve. According to a still another embodiment, the spikes 22 formed by filaments of the material mesh are configured to vary their angle of extension from the sleeve in dependence of the diameter of the sleeve 19. In particular, the filaments may be configured so that the angle of extension of the spikes 22 is at a minimum with regard to the longitudinal axis of the sleeve 19 when the sleeve 19 has its maximum diameter, for example, when no pressure is applied, and so that the angle of extension of the spikes is at a maximum with regard to the longitudinal axis of the sleeve 19, when the sleeve 19 has a larger diameter, for example, when a pressure is applied that fits the diameter of the sleeve 19 to the outer diameter of the hollow organ.

FIG. 3 shows a fitting 13 according to a particular embodiment of the invention. The fitting 13 is formed by a flat ring having a slit in the longitudinal direction so that it can be bend and opened as is visible in FIG. 3a in order to fix it around two hollow organ 5 ends provided with sleeves 19 as shown in FIG. 3b. In the fitting 13, a number of windows 23 or openings are provided that permit to observe the contact between the hollow organ 5 ends. By closing the fitting 13 on the connected hollow organ 5 ends as is shown in FIG. 3d, a stable connection of the hollow organ 5 ends is achieved. As is visible in FIG. 3c, the fitting 13 can be formed of a spring material that can be opened against its spring tension and automatically closes on the connected hollow organ 5 ends when the bending force is released. The fitting 13 may also be formed by a biodegradable or biocompatible plastic material. In particular, it may be formed by magnesium covered with biodegradable plastic. The fitting 13 may also be formed by metal or any other suitable material.

Figure 4:
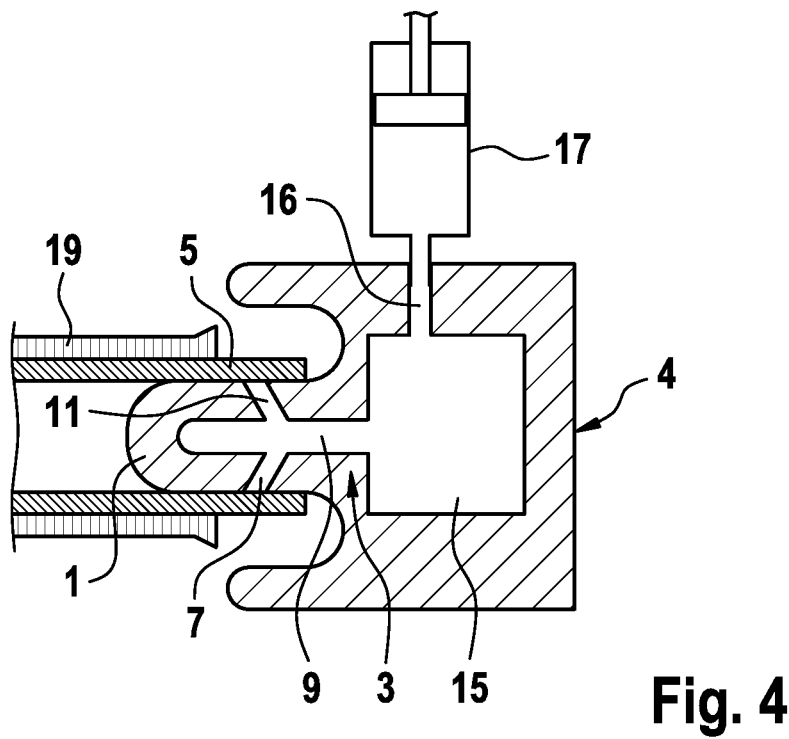
FIG. 4 shows a turning-over device, according to one embodiment of the invention, in a state at which the pin of the front part of the turning-over device is inserted in the hollow organ and the end of the blood vessel butts against the rear part of the turning-over device.

FIG. 4 shows the turning-over device according to one embodiment of the invention, wherein a pin 1 of a front part 3 of the turning-over device is inserted into a hollow organ 5 so that the end of the hollow organ 5 abuts against a concave part of a rear part 4 of the turning-over device from which the pin 1 of the front part 3 projects. The pin 1 comprises an annular outlet 7 provided in the pin 1 perpendicular to its longitudinal axis of extension. Furthermore, a central conduit 9 coinciding with the longitudinal axis of symmetry of the pin 1 is provided in the pin 1 which branches off into a branch conduit 11 that ends in the annular outlet 7. The branch conduit 11 branches off from the central conduit 9 at an angle of about 50 degrees. While the central conduit 9 traverses basically the entire pin 1 and terminates in a dead end, the branch conduit 11 branches off from the central conduit 9 at approximately half of its length. Furthermore, in the rear part 4 of the turning-over device, a reservoir 15 is provided which is connected to the central conduit 9. The reservoir 15 is configured to receive a fluid that can be pressurized and ejected through the outlet 7. In order to pressurize the fluid, the reservoir 15 comprises a channel 16 with an opening to the outside of the rear part 4. A means for pressurizing a fluid in the reservoir 15 such as a syringe 17 or a catheter may be connected to the channel 16. Preferably, the fluid used in the turning-over device is a biocompatible fluid such as a saline solution. Furthermore, as is visible in FIG. 4, a sleeve 19 has been pushed over the end of the hollow organ 5 in such a way that the sleeve 19 partly overlaps with the tip of the pin 1 but does not cover its outlet 7. The end of the hollow organ 5 is arranged between the sleeve 19 and the pin 1 so that it extends over the entire length of the pin 1 up to the concave part of the rear part 4 of the turning-over device.

Figure 5:
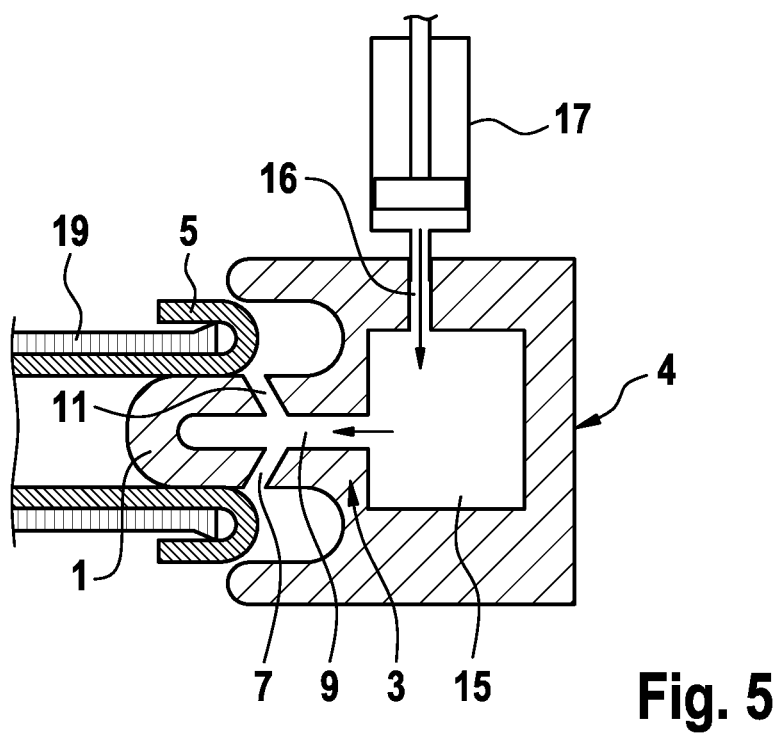
FIG. 5 shows the turning-over device of FIG. 4 in a state when the end of the hollow organ is completely folded back on the sleeve.

Pressurizing the fluid in the reservoir 15 with a pressurizing means causes the fluid to exit the annular outlet 7. The jet of pressurized fluid impinges on the inner side of the hollow organ 5 along a basically circular line and turns the end of the hollow organ 5 over the end of the sleeve 19 so that the end of the hollow organ 5 is folded back on the sleeve 19 as is shown in FIG. 5. Preferably, the diameter of the sleeve 19 approximately corresponds to the outer diameter of the hollow organ 5, while the outer diameter of the pin 1 approximately corresponds to the inner diameter of the hollow organ 5.

Figure 6:
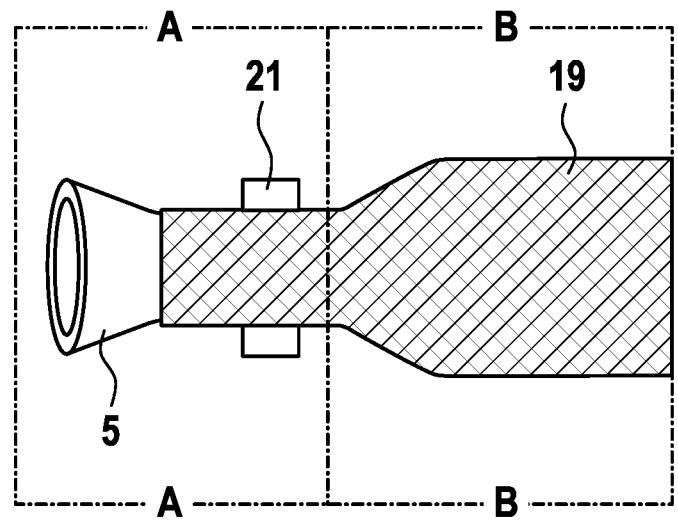
FIG. 6 shows the turning-over device and the hollow organ with the end of the hollow organ folded back on a sleeve according to an embodiment of the invention.
Figure 6:
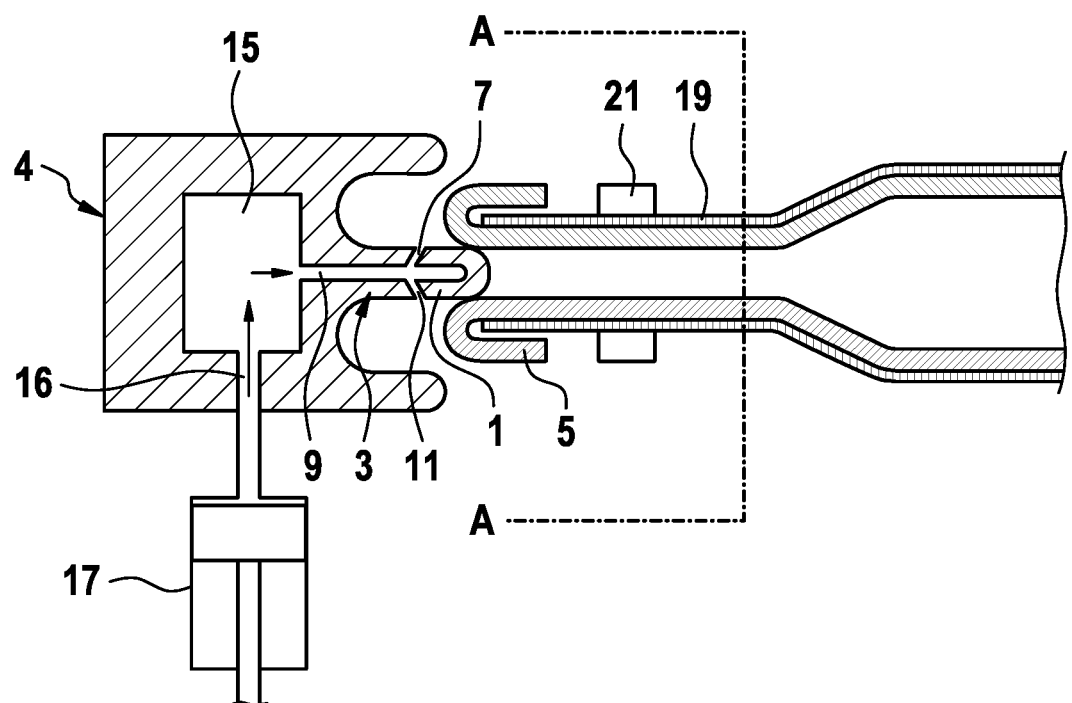

FIG. 6 shows the turning-over device in combination with a sleeve 19 according to a particular embodiment that has an adjustable diameter. As is visible in FIG. 4, the sleeve 19 consists of a mesh of filaments of a self-expandable material. By means of a clamping device 21 (e.g. forceps) exerting a radial pressure on the sleeve 19, the diameter of the sleeve, which has been pushed over the hollow organ 5, is reduced and adjusted to the outer diameter of the hollow organ 5. As is visible in FIG. 6, the diameter of the sleeve 19 is only adjusted in section A on the left side of the sleeve 19, while the diameter of the sleeve 19 on the right side in section B which has not been compressed is significantly larger and corresponds to the unrestricted diameter of the mesh. Accordingly, the sleeve 19 formed of a self-expandable material mesh can be adjusted exactly to the diameter of the hollow organ 5, and subsequently the end of the hollow organ 5 can be turned over with the turning-over device and folded back on the sleeve 19. Once the end of the hollow organ 5 is turned over on the sleeve, the pressure exerted by the clamping device 21 can be released and the sleeve 19 will be held in the compressed shape by the back-folded hollow organ 5 end.

Figure 7:
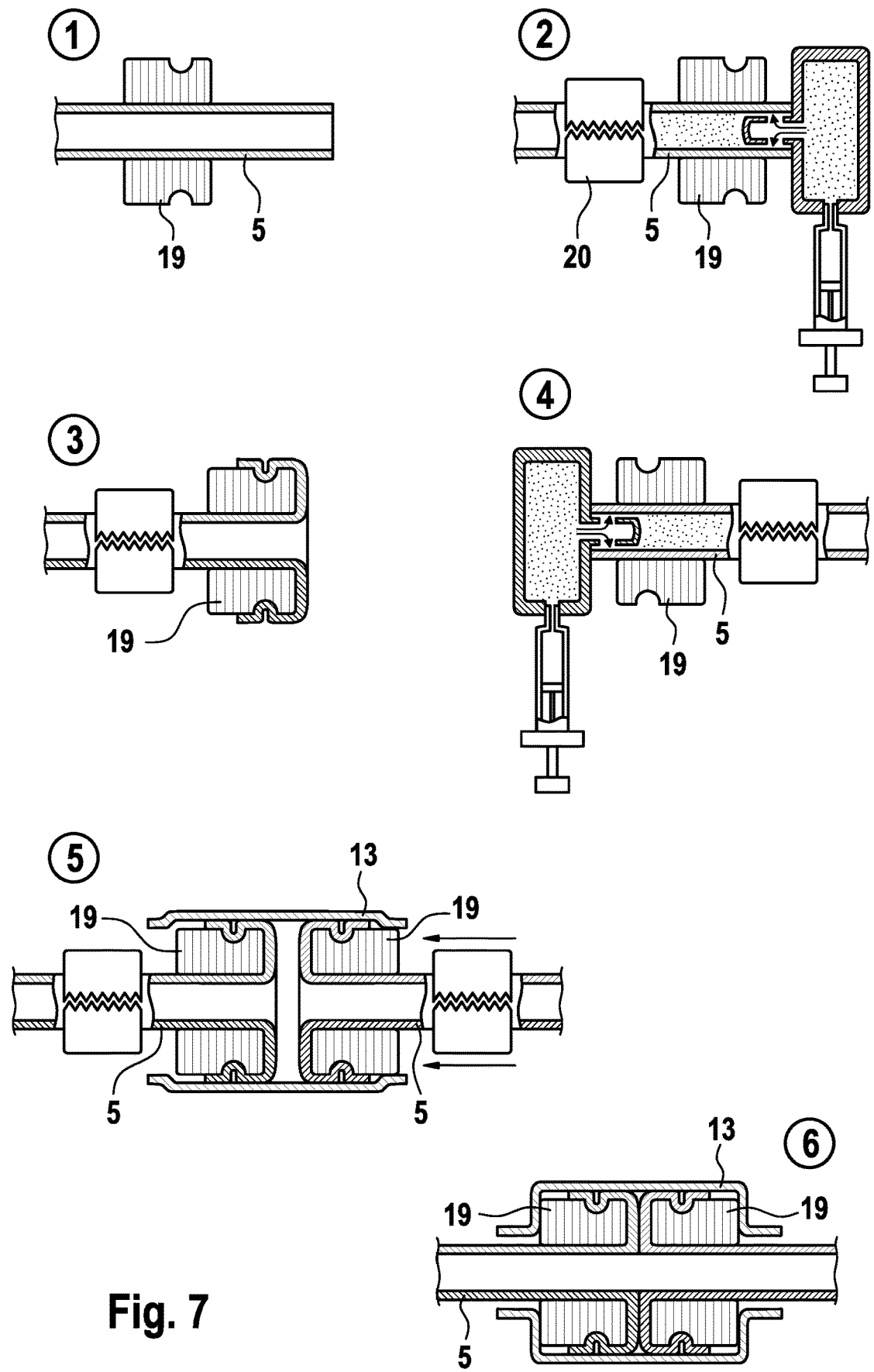
FIG. 7 shows a sequence of steps of connecting two hollow organ ends.

FIG. 7 schematically shows the procedural steps of connecting two hollow organ 5 ends according to one example. In a first step 1, a sleeve 19 is pushed over the hollow organ 5 end, wherein a defined length of the hollow organ 5 end projects from the sleeve 19. The sleeve 19 may be a sleeve 19 with a fixed diameter or a sleeve 19 having an adjustable diameter, wherein the sleeve 19 is preferably uncompressed during the positioning on the hollow organ 5. As shown in step 2, the length of the hollow organ 5 end projecting from the sleeve 19 basically corresponds to the distance between the proximal end of the pin 1 and the outlet 7 provided in the pin 1, wherein the sleeve 19 does not overlap the outlet 7 but just the portion of the pin at its distal end. Furthermore, a clamp 20 is provided on the hollow organ 5 behind the sleeve 19. Subsequently, a biocompatible fluid such as a saline solution is pressurized by means of a syringe 17, is ejected from the outlet 7 of the pin 1 and turns over the end of the hollow organ 5 so that it is folded back on the sleeve 19 as is visible in step 3. Subsequently, a second hollow organ 5 end is prepared in the same manner as shown in step 4. In step 5, the two hollow organ 5 ends folded back on respective sleeves 19 are introduced into a common fitting 13 and latched therein. In the fitting 13, the inner sides of the hollow organ 5 ends get into contact with each other and are fixed in this position. Accordingly, a re-established hollow organ 5 such as a blood vessel is provided.

Numerous modifications may be provided to the shown embodiments without departing from the scope of the invention.

The invention claimed is:

1. A turning-over device for turning-over an end of a hollow organ around an end of a sleeve, comprising
   a front part consisting of a pin having a diameter which is configured to correspond approximately to an inner diameter of the hollow organ, and
   a rear part having a diameter which is larger than that of the front part,
   wherein the rear part comprises a fluid connection to at least one outlet of the device for a fluid that during a turning-over process is pressed out of said at least one outlet, and
   wherein said at least one outlet is formed in a sidewall of said pin, said sidewall being proximal to a tip of said pin, and wherein the fluid is pressed out of said pin at least partly under a nonzero angle in relation to an axis of extension of said pin.

2. The device according to claim 1,
   wherein said pin comprises a rotationally symmetrical body, and
   wherein said at least one outlet is formed in a wall of said rotationally symmetrical body.

3. The device according to claim 1, wherein said at least one outlet comprises an annular shape and extends perpendicularly to an axis of symmetry of said pin over more than half of its periphery.

4. The device according to claim 1, wherein the device is configured so that a mean angle at which the fluid exits the at least one outlet with relation to the axis of extension of said pin is between 10 and 90 degrees.

5. The device according to claim 1,
   wherein the at least one outlet is positioned at a predetermined distance along a length of the pin, and
   wherein the pin is configured to be pushed into an opening of the hollow organ so that the at least one outlet is covered by the hollow organ when an edge of the hollow organ is pushed over the pin towards the rear part of the device.

6. The device according to claim 1, wherein a position of said at least one outlet is spaced from a distal end of the pin by a predetermined distance along which the hollow organ can be clamped between the pin and the sleeve that has been pushed over the hollow organ.

7. The device according to any claim 1,
   wherein the pin comprises a central conduit that essentially extends in its longitudinal direction to connect the front part of the device with the rear part, and
   wherein said central conduit branches off in at least one branch conduit that is connected with the at least one outlet.

8. The device according to claim 7, wherein the at least one branch conduit branches off from said central conduit in direction of a distal end of the pin with an angle between 10 and 90 degrees.

9. The device according to claim 1, wherein a front side of the rear part of said device, said front side being configured to face towards an opening of the hollow organ, has a concave part.

10. The device according to claim 1,
    wherein the rear part of said device comprises a reservoir for the fluid, and
    wherein the rear part has an opening through which the fluid in the reservoir can be pressurized.

* * * * *